US008621234B2

(12) United States Patent
Qu et al.

(10) Patent No.: US 8,621,234 B2
(45) Date of Patent: Dec. 31, 2013

(54) INFORMATION INTERCHANGE SYSTEM AND APPARATUS

(75) Inventors: Jin Qu, Shanghai (CN); Hui Li, Shanghai (CN); Milan Petkovic, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 514 days.

(21) Appl. No.: 12/810,023

(22) PCT Filed: Dec. 26, 2008

(86) PCT No.: PCT/IB2008/055541
§ 371 (c)(1),
(2), (4) Date: Sep. 29, 2010

(87) PCT Pub. No.: WO2009/083922
PCT Pub. Date: Jul. 9, 2009

(65) Prior Publication Data
US 2011/0016328 A1    Jan. 20, 2011

(30) Foreign Application Priority Data
Dec. 28, 2007   (CN) .......................... 2007 1 0306619

(51) Int. Cl.
*H04L 29/06* (2006.01)

(52) U.S. Cl.
USPC ........................................... 713/189; 726/27

(58) Field of Classification Search
USPC ........................................... 713/189; 726/27
See application file for complete search history.

(56) References Cited

U.S. PATENT DOCUMENTS

| | | | |
|---|---|---|---|
| 2002/0073138 A1* | 6/2002 | Gilbert et al. ................. | 709/201 |
| 2004/0215981 A1 | 10/2004 | Ricciardi et al. | |
| 2005/0043964 A1* | 2/2005 | Thielscher et al. ............... | 705/2 |
| 2005/0236474 A1 | 10/2005 | Onuma et al. | |
| 2007/0027715 A1 | 2/2007 | Gropper et al. | |
| 2007/0130465 A1* | 6/2007 | Zeng et al. .................... | 713/171 |
| 2008/0320035 A1* | 12/2008 | Riedl et al. ................ | 707/103 R |
| 2009/0265788 A1* | 10/2009 | Ehrenschwender et al. .... | 726/26 |
| 2011/0072142 A1* | 3/2011 | Herz et al. .................... | 709/229 |

FOREIGN PATENT DOCUMENTS

WO        2005088899 A1    9/2005

OTHER PUBLICATIONS

Yang et al: "A Smart-Card Enabled Privacy Preserving E-Prescription System"; IEEE Transactions on Information Technology in Biomedicine, Vol. 8, No. 1, Mar. 2004, pp. 47-58.
De Meyer et al: "Electronic Signature and Certification Models in Health Care"; MEDINFO 2001, pp. 1252-1256.
Smith: "Pets to the People: The Role of Data Protection Agencies in the Distribution of Information on Pets on the Internet to the Public"; Thesis for University of Oslo, 95 Page Document.

* cited by examiner

*Primary Examiner* — Jeffrey Pwu
*Assistant Examiner* — William Corum, Jr.

(57) ABSTRACT

To overcome the drawback of difficulties when interchanging a patient's health record among different health information management systems and yet keep the patient's privacy, this invention proposes a method comprising the steps of: extracting, from a certificate, a signature of a first service provider and a first identifier; generating a second identifier corresponding to the first identifier; sending a request to any one of a second identifier manager and the first service provider so as to request a record associated with the first identifier; receiving the requested record from any one of the second identifier manager and the first service provider; and associating the requested record with the second identifier. Use of the proposed method provides the advantage that there is no need to unify all health information management systems adopting the same pseudonymization service, and makes it easy to share health information among different health information management systems without disclosing the patient's privacy.

25 Claims, 4 Drawing Sheets

Certificate
{
    Pseudo identifier;
    Public key of public key pair (optional);
    Additional dataset (optional);
    Signature of pseudonymization service;
}

INFORMATION INTERCHANGE SYSTEM AND APPARATUS

FIELD OF THE INVENTION

This invention relates to information interchange systems, particularly to systems and apparatus for interchanging health information among different health information management systems.

BACKGROUND OF THE INVENTION

In recent years, health and/or medical information management systems have been established all over the world. Managing patients' health information and privacy among these health information management systems has become a very important issue. After the Health Insurance Portability and Accountability Act (HIPAA) was enacted by US Congress in 1996, researchers, physicians and medical centers became more careful to deal with the data of patients, including patients' health information and privacy.

According to ISO, anonymization is the process that removes the association between the identifying data set and the data subject. Pseudonymization is a particular type of anonymization that removes the association between the identifying data set with a data subject and adds an association between a particular set of characteristics relating to the data subject and one or more pseudonyms. Pseudonymization is recognized as an important method of protecting the privacy of patients. ISO/TC 215 is developing a new specification "Pseudonymization practices for the protection of personal health information and health related service" (ISO/DTS 25237), which focuses on principles and requirements using the pseudonymization service for the protection of personal health information.

Based on ISO/DTS 25237, HITSP (Healthcare Information Technology Standards Panel) developed architecture, illustrated in FIG. 1, for implementing pseudonymization. In the architecture 100, four entities are included, namely the patient, the hospital, the PIX (Patient Identifier Cross-reference) manager and the Pseudonymization service provider. In step 110, the hospital provides a registration service for the patient. In step 120, the hospital subsequently sends patient information to the PIX manager. The patient information may only include the patient's real identifier (patient's name and ID number) and the patient's record ID which can be used in this hospital, or it may include more information, such as the address, contact information, etc. In step 130, the PIX manager records the patient identifier. In this step, the PIX manager also associates the patient identifier with at least one of additional information components contained in the patient information sent from the hospital, such as the patient's health record ID, address, contact information, etc. In step 140, the PIX manager sends a request for a pseudo identifier to the pseudonymization service provider. Upon receiving the request, the pseudonymization service provider assigns, in step 150, a pseudo identifier for the patient and, in step 160, returns the pseudo identifier to the PIX manager. Then the PIX manager stores and associates the pseudo identifier with the patient's identifier. Optionally, the PIX manager can also associate the pseudo identifier with the patient information received from the hospital, e.g. the patient's ID, address and contact information, etc. In step 180, the PIX manager prepares a pseudo certificate for the patient and sends it to the hospital. In step 190, the hospital records the certificate and, in step 195, sends the certificate to the patient. After receiving the certificate, the patient can use this certificate in this hospital and other hospitals understanding the format of this certificate. By using this certificate, the patient can obtain service from the hospitals understanding the format and content of this certificate and avoid disclosing his real identifier.

However, with the precondition of a unique pseudonymization service available for all the entities in different hospitals, the architecture 100 can only be used in one health/medical information management system/domain, in which all the hospitals can recognize this certificate including pseudo identifiers issued by a common pseudonymization service provider. Currently, people have more and more possibilities to visit different hospitals in different cities, or even different countries. It is unreasonable to assume that different hospitals in different cities and different countries adopt a common pseudonymization service. The patient therefore has to re-register a new identifier or certificate in each health/medical service provider system. Since there is no method of interoperability between different systems, it is difficult for patients to re-use their previous health/medical information stored in different systems.

Therefore, there is a need to provide methods that are capable of interchanging health/medical information among different health/medical information management systems, which adopt different pseudonymization services.

SUMMARY OF THE INVENTION

It is an object of the invention to provide methods and apparatus for interchanging information, especially health/medical information among different health/medical information management systems, especially those systems using different pseudonymization services.

According to one embodiment of the invention, the object and several other objects are obtained in a first aspect of the invention by providing an information interchange system. The information interchange system comprises: a reader configured to read a certificate comprising a first identifier and a signature; a reader configured to extract, from a certificate, a signature of a first service provider and a first identifier and generate a second identifier corresponding to the first identifier; a first identifier manager configured to associate the first identifier with the second identifier and send a request to any one of a second identifier manager and the first service provider so as to request a record associated with the first identifier; a receiver configured to receive the requested record from any one of the second identifier manager and the first service provider and associate the received record with the second identifier.

The record associated with the first identifier includes any one of a medical record, a disease history, and other health/medical information relating to the patient identified by the first identifier, but does not include the patient's real identifier, such as his identification number, driver license number, insurance number, or medical registration number which can easily reverse the patient's real identity.

This system, used for a current health/medical information management system, has the advantage that health information, for example, the record associated with the first identifier, is obtained from another health/medical information management system without the need for the current health/medical information management system to recognize the certificate issued by another system. In the current system, the second identifier can be associated with the patient's previous record. Records can thus be interchanged among different systems without the need for a unique pseudonymization service.

Optionally, the second identifier manager further comprises: an identifier mapping unit configured to map the first identifier to a third identifier; a database configured to retrieve a record associated with the third identifier; a sender configured to send the retrieved record to the receiver as being the record associated with the first identifier.

The third identifier may be the patient's real identity, such as his identification number, driver license number, insurance number, or medical registration number, so that the record associated with his real identity can be found. The database may be a standalone database or a separate hospital storing a patient's real identity and record.

Optionally, the third identifier may also be a pseudo identifier generated by a pseudonymization service provider. The second identifier manager, which may be a PIX manager, can also use this pseudo identifier to retrieve a record from the database.

Alternatively, when the second identifier manager finds that the third identifier was issued by another health/medical information management system using another pseudonymization service which it does not support but can extract the information about the other pseudonymization service provider, the first identifier can send the third identifier to the other pseudonymization service so as to request a record. By using this recursive method, it is possible to find the initial system that stored the patient's health record, irrespective of whether the certificate held by the patient was issued by any other health/medical information management system.

Optionally, the information interchange system further comprises a second service provider configured to generate identifiers, wherein any one of the reader and the first identifier manager is further configured to request a fourth identifier from the second service provider, and the reader is further configured to set the received fourth identifier as the second identifier. Furthermore, the second service provider is further configured to generate a second certificate which can be used by the patient in the current health information management system. The patient can also bring this second certificate to another health information management system, which can obtain a record from the current health information management system by using the above-mentioned methods.

The first identifier and the second identifier may be pseudo identifiers for identifying a patient without disclosing his real identity. The patient's privacy is protected in both health information management systems.

The signature generated by the first service provider provides information about at least one of the second identifier manager and the first service provider, e.g. a pseudonymization service provider.

According to another embodiment of the present invention, it is a second aspect of the invention to provide a card for storing a certificate configured to identify a patient, wherein the certificate comprises: a first pseudo identifier generated by a pseudonymization service provider and configured to be used in a health information management system; and a signature of a pseudonymization service provider, configured to contain information about at least one of the pseudonymization service provider and an identifier manager, wherein the identifier manager is configured to identify the first pseudo identifier.

Since the patient's real identity is not contained in this card, his privacy is protected. In combination with the methods disclosed above, the patient's record can be found and used in the current health information management system.

To further enhance the security of the certificate, i.e. to check the link between the certificate and the person holding this certificate, i.e. whether the certificate belongs to this person, the certificate may optionally further comprise a public key of a public key pair. The public key is used to verify the patient's signature. Since, in this certificate, the public key is associated with the pseudo identifier of the patient, the patient uses the private key of the public key pair to sign some documents, and the other party uses the public key in the above certificate to verify the signature without disclosing the patient's real identity. The public key can be used online, e.g. through the Internet.

In another embodiment, an additional dataset may be comprised in the certificate so as to enhance security. The additional dataset may be a hash of a secret s, wherein the s may be a parameter known by the patient, personal information of the patient, or the patient's real identity. As the hash function is a one-way function for which there is zero-knowledge proof, the patient can prove to the other party, e.g. a doctor, that the certificate with his pseudonym is indeed his, without revealing his identity.

In another embodiment, an additional dataset may comprise at least one biometrical parameter representing the patient. The biometrical parameter, such as a fingerprint, can be used to verify the patient holding the certificate. It is an additional advantage that the biometrics is always carried by the patient. The biometrics is not stored in a public database and therefore cannot be linked to the patient's real identity, while it keeps the function of proving ownership of the certificate.

According to another embodiment, a third aspect of the invention is achieved by providing a method of obtaining information, especially among different health/medical information management systems. The method comprises the steps of:
  a) extracting, from a certificate, a signature of a first service provider and a first identifier;
  b) generating a second identifier corresponding to the first identifier;
  c) sending a request to any one of a second identifier manager and the first service provider so as to request a record associated with the first identifier;
  d) receiving the requested record from any one of the second identifier manager and the first service provider; and
  e) associating the requested record with the second identifier.

According to another embodiment, it is a fourth aspect of the invention to provide a method of generating a second certificate, especially without the need of knowing the patient's real identity. The method comprises the steps of:
  a) extracting, from the first certificate, a signature of a first service provider and a first identifier;
  b) checking the validity of the first identifier on the basis of at least one of the signature of the first service provider and the first identifier; and
  c) generating the second certificate comprising a second identifier and signature of a second service provider, wherein the second identifier corresponds to the first identifier.

Use of this method provides the advantage that a new certificate comprising a pseudo identifier can be created without knowing the patient's real identity.

To enhance security, the second certificate may optionally further comprise any one of a public key, a hash of secret s, biometrical parameters, and other information which can be used to verify ownership of the second certificate.

Optionally, the method further comprises a step of associating the record associated with the first identifier with the second identifier as being the record associated with the second identifier.

These and other aspects, features and/or advantages of the invention are apparent from and will be elucidated with reference to the embodiments described hereinafter.

BRIEF DESCRIPTION OF THE DRAWINGS

Embodiments of the invention will be described, by way of example only, with reference to the drawings, in which.

DESCRIPTION OF EMBODIMENTS

Figures 1, 2:
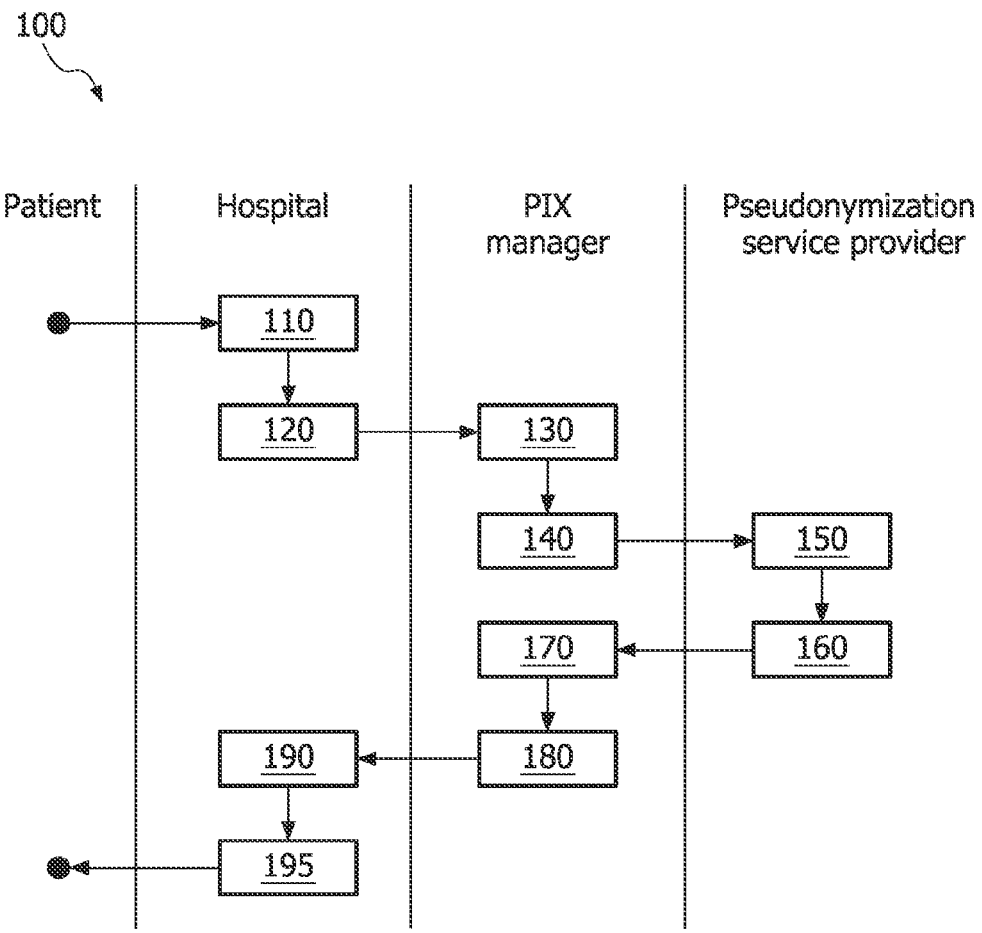
FIG. 1 illustrates the architecture developed by HITSP.
FIG. 2 illustrates a certificate according to one embodiments of the invention.

FIG. 2 illustrates, by way of example, an embodiment of content of a certificate. The certificate comprises a pseudo identifier and a signature of a pseudonymization service. The pseudo identifier is generated by a pseudonymization service provider and used to identify the patient in a current health/medical information management system, e.g. a hospital in which the patient registers. It is not possible to deduce the patient's real identity from the pseudo identifier only. The signature of the pseudonymization service is generated by the pseudonymization service provider and can be used to validate the pseudo identifier. The certificate can also be used to deduce the information about the pseudonymization service provider. Optionally, the certificate can be further used to deduce information about an identifier manager, e.g. a PIX manager, in which the patient's one previous identifier and the association between the previous identifier and the new pseudo identifier generated by the current pseudonymization service provider are stored. The previous identifier may be the patient's real identity, in which case the hospital is the first registered hospital for the patient. The previous identifier may also be a pseudo identifier generated by another pseudonymization service provider, in which case the current hospital is not the first registered hospital for the patient, and the patient bringing a certificate comprising a pseudo identifier comes to the current hospital. In the latter case, it is possible to use a recursive method to deduce the first registered hospital for the patient.

In another embodiment, the certificate may optionally comprise a public key of a public key pair. Since, in the certificate, the public key is associated with the patient's pseudo identifier, the patient can use the private key of the public key pair to sign some document, and another person can use the public key to verify the signature of the patient without disclosing his real identification. It is an advantage to use the public key to verify the patient online, e.g. through the Internet or a dedicated intranet. In this case, the public key is optionally taken into consideration when generating the signature of the pseudonymization service, which further enhances the security of the certificate.

In another embodiment, the certificate optionally comprises an additional dataset which is used to enhance the security that the certificate belongs to the patient. In this case, the additional dataset is optionally taken into consideration when generating the signature of the pseudonymization service, which further enhances the security of the certificate. It is advantageous that the doctor can ascertain whether he is dealing with the right patient and the right health record. The additional dataset may be a hash of a secret s, which is known by the patient. The secret s may be a predefined parameter known by the patient, the patient's real identity, or personal information of the patient, e.g. his name, birthday, passport number, etc. Since the hash function is a one-way function for which there is zero-knowledge proof, the patient can prove to the doctor that the certificate with his pseudonym is indeed his, without revealing his identity. It is almost impossible to deduce the patient's real identity from the result of the hash function.

In another embodiment, the additional dataset optionally comprises one or more biometrical parameters. The biometrical parameters, such as fingerprint, iris, etc. are used to describe the patient's physiological character features, and are not stored in public databases. This implementation has two advantages. The first is that the biometrical parameters are always available from the patient's body, and the second is that the biometrics cannot be linked to the patient's real identity and is difficult to forge.

It is also possible to incorporate both a public key and an additional dataset in a certificate.

Figure 3:
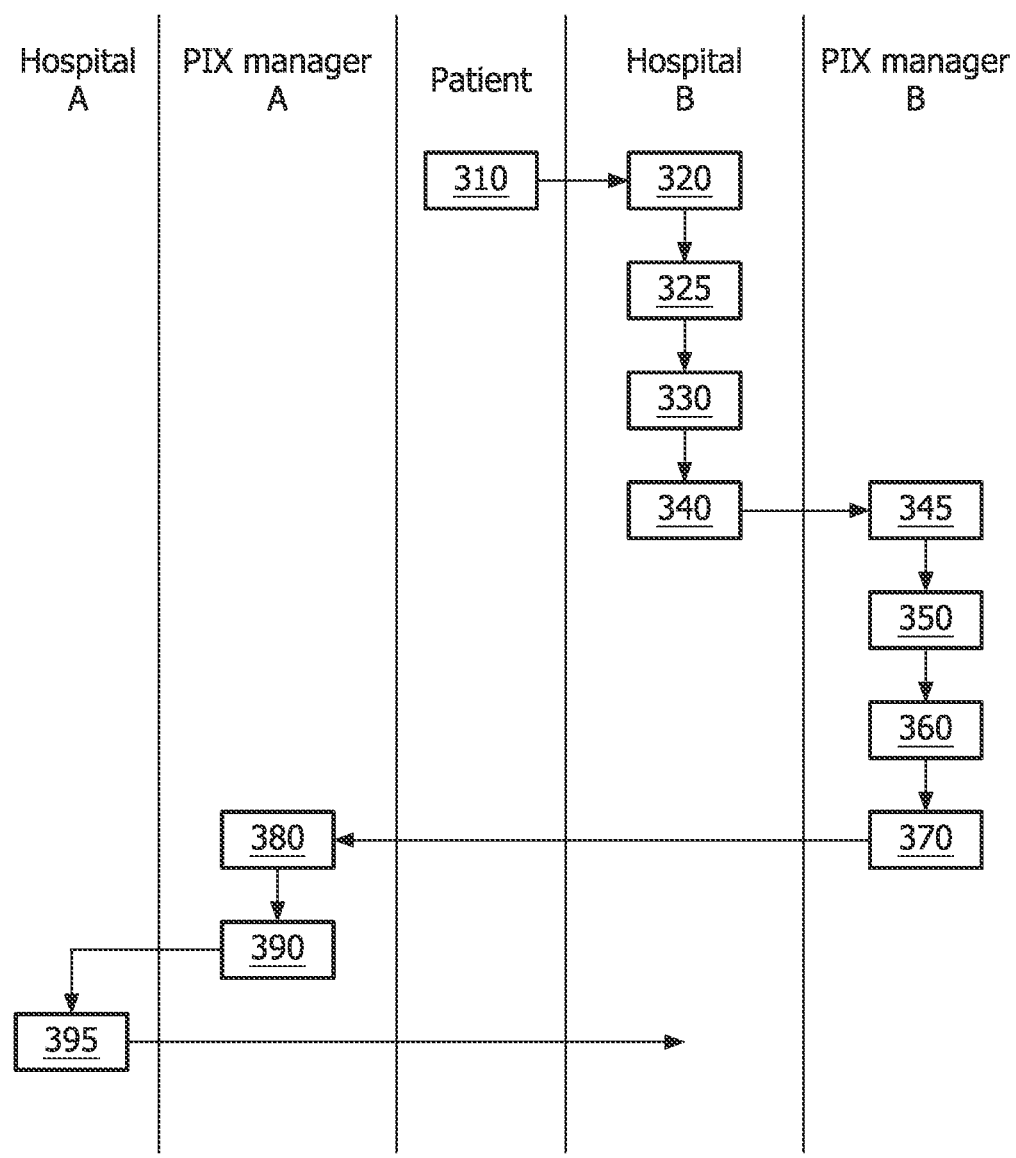
FIG. 3 illustrates an information interchange process according to one embodiment of the invention.

The certificate illustrated in FIG. 2 can be used in FIG. 3, which illustrates an information interchange process according to one embodiment of the invention. Let us assume that the patient has registered in hospital A and PIX manager A, and has obtained a certificate comprising a pseudo first identifier and signature of the pseudonymization service, issued by a first pseudonymization service provider. Now the patient visits a hospital in another city or country, which adopts a different pseudonymization service and a different pseudo identifier system. It is troublesome for the patient to use his original certificate in the hospital he is now visiting, e.g. hospital B and PIX manager B. In step 310 of the information interchange process, the patient first registers in hospital B by using his original certificate. In hospital B, there is a reader configured to read the certificate and extract the signature of the first service provider and the first identifier. In step 320, the reader extracts the first identifier and the signature. It is optional for the reader to check the validity of the first identifier on the basis of the signature or to send the first identifier and the signature to another entity so as to validate the first identifier. In step 330, a second pseudo identifier is generated, which can be used in hospital B and PIX manager B. In step 340, the first identifier, the second identifier, and the signature of the first service provider are sent to a first identifier manager, e.g. PIX manager B. It is optional to check the validity of the first identifier in PIX manager B in step 345 on the basis of the signature of the first service provider. In step 350, PIX manager B associates the second identifier with the first identifier. Actually, the first identifier is a pseudo identifier used by the patient in hospital A/PIX manager A, while the second identifier is another pseudo identifier used by the same patient in hospital B/PIX manager B. In step 360, PIX manager B extracts information about the second identifier manager, e.g. PIX manager A, based on the certificate. It also allows extracting the information from the first identifier and/or the signature of the first service provider. In step 370, PIX manager B requests the original record associated with the first identifier from the first identifier manager, e.g. PIX manager A. At least the first identifier is included in the request. It is also practical for PIX manager B to request the first service provider to find the record of the first identifier and send it back to PIX manager B. It provides an additional advantage, especially when PIX manager B cannot deduce the second identifier manager. Since the certificate is generated by the first service provider after the patient has registered in hospital A/PIX manager A, it is easy for the first service provider to find hospital A and PIX manager A. Upon receiving the request from PIX manager B, an identifier mapping unit of the PIX manager A maps the first identifier to a third identifier in step 380, and sends a request to a database, e.g. an element in hospital A, to request the record associated with the third identifier in step 390. After the record associated with the third identifier is retrieved, a sender in the second identifier manager sends, in step 395, the retrieved record as the requested record associated with the first identifier to a receiver which is located in hospital B.

The embodiment illustrated in FIG. 3 clearly shows that the patient's real identity can never be sent to the visited hospital, e.g. hospital B/PIX manager B. The patient's privacy is thus protected while the necessary health record is utilized in the later diagnosis.

In the embodiment illustrated in FIG. 3, the third identifier found by the identifier mapping unit in the second identifier manager may be the patient's real identity, but may also be another pseudo identifier which is used by the patient in hospital A. When the third identifier is a pseudo identifier, hospital A/PIX manager A can use a similar method as disclosed in the embodiment of FIG. 3 so as to find another hospital/PIX manager which issues and uses the pseudo identifier. Irrespective of the number of pseudo identifiers the patient uses, use of the recursive method makes it easy to locate the hospital holding the patient's health/medical record.

Figure 4:
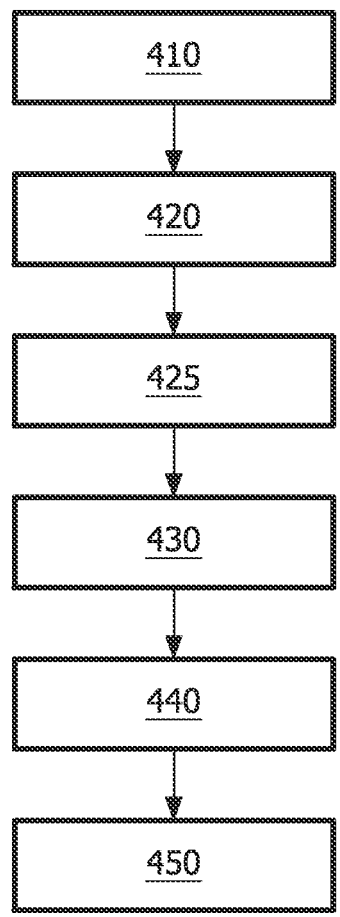
FIG. 4 illustrates a method of generating a certificate according to one embodiment of the invention.

In the embodiment illustrated in FIG. 3, the second identifier is generated by the reader in step 330. It is also practical to generate the second identifier by using the method disclosed in the embodiment illustrated in FIG. 4. After the signature of a first service provider and a first identifier is extracted by the reader in step 410, the reader sends a request to a second pseudonymization service provider so as to generate a second pseudo identifier, in step 420. In step 430, the second pseudonymization service provider generates a second pseudo identifier, which can be understood by hospital B and PIX manager B, and sends it back to the reader. Optionally, validities of the first identifier and the signature of the first service provider are checked in step 425. If the validity check fails, it is reasonable to reject the request and indicate the reason to the reader, e.g. the certificate is faked. The reader associates the second identifier with the first identifier in step 440. Until now, the second identifier associated with the patient has been generated and can be used in hospital B. After the record associated with the first pseudo identifier is available, it is easy to associate the record with the second identifier, in step 450, so that the patient's previous record is usable in hospital B. It is noted that the patient's real identity is not disclosed.

Figure 5:
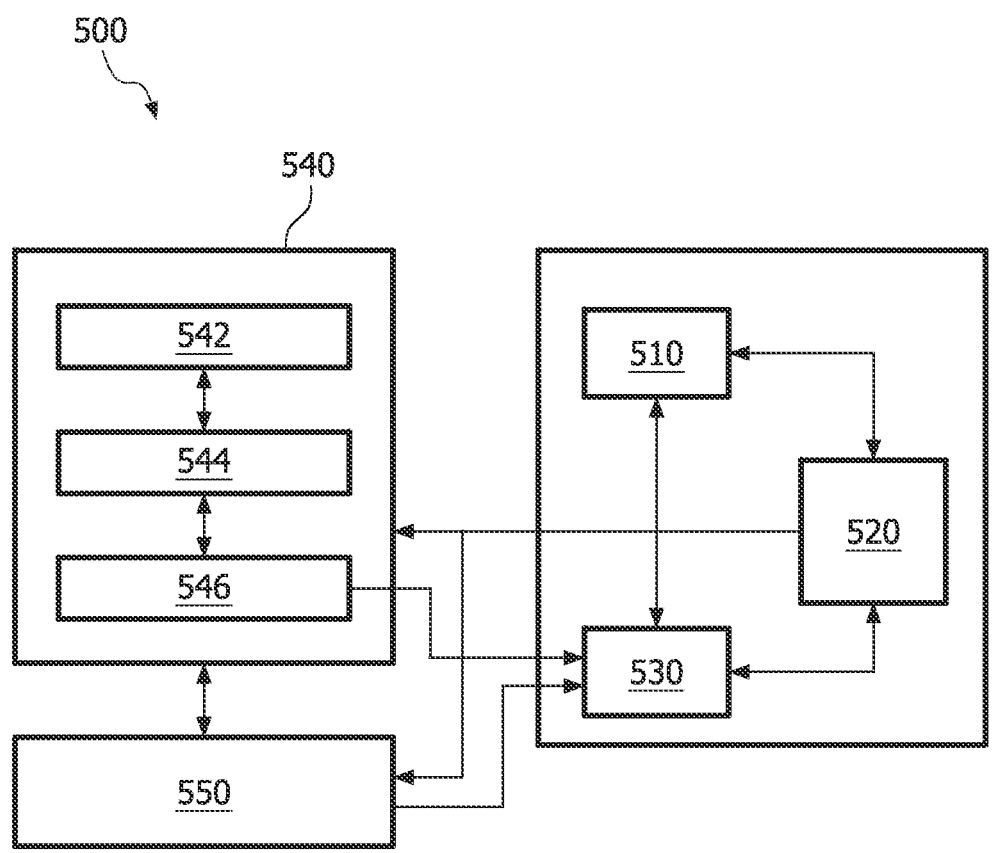
FIG. 5 is a block diagram of an information interchange system according to one embodiment of the invention.

FIG. 5 illustrates, by way of example, an information interchange system according to one embodiment of the invention. The information interchange system 500 comprises a reader 510, a first identifier manager 520 and a receiver 530. The reader 510 is configured to extract a signature of a first service provider and a first identifier from a certificate and generate a second identifier corresponding to the first identifier. The first identifier manager 520 is configured to associate the first identifier with the second identifier and send a request to any one of a second identifier manager and the first service provider so as to request a record associated with the first identifier. Information about the second identifier manager can be deduced from the first certificate, e.g. from the first identifier, the signature of the first service provider, or the combination. The receiver 530 is configured to receive the requested record from any one of the second identifier manager and the first service provider, and associate the requested record with the second identifier.

The system 500 may further comprise the second identifier manager 540, which further comprises a mapping unit 542, a health/medical information database 544 and a sender 546. The mapping unit 542 is configured to map the first identifier comprised in the request sent from the first identifier manager to a third identifier. The database 544 is configured to retrieve the record associated with the third identifier. The sender 546 is configured to send the retrieved record to the receiver as the requested record associated with the first identifier.

Optionally, the system 500 further comprises the first service provider 550, which generates the pseudo identifier and the certificate. The first service provider 550 is further configured to receive the request from the first identifier manger 520 and find a third identifier corresponding to the first identifier comprised in the received request. The first service provider 550 then requests the second identifier manager 540 to find the record associated with the third identifier. Subsequently, the record associated with the third identifier can be sent from the first service provider 550 to the receiver 530 as the record that is associated with the first identifier.

By utilizing the methods and apparatus disclosed in the embodiments of the invention, it is easy to achieve the object of interchanging information, e.g. health/medical records among different health/medical information management systems while preventing disclosure of the patient's privacy.

The invention can be implemented in any suitable form including hardware, software, firmware or any combination of these. The invention or some of its features can be implemented as computer software. The elements and components of an embodiment of the invention may be physically, functionally and logically implemented in any suitable way. Indeed, the functionality may be implemented in a single unit, in a plurality of units or as part of other functional units. As such, the invention may be implemented in a single unit, or may be physically and functionally distributed between different units and processors.

Although the present invention has been described with reference to the specified embodiments, it is not intended to be limited to the specific form set forth herein. Rather, the scope of the present invention is limited only by the accompanying claims. In the claims, use of the verb "comprise" and its conjugations does not exclude the presence of other elements or steps. Although individual features may be included in different claims, these may possibly be advantageously combined, and the inclusion in different claims does not imply that a combination of features is not feasible and/or advantageous. In addition, singular references do not exclude a plurality. Thus, references to "a", "an", "first", "second" etc. do not preclude a plurality. Furthermore, reference signs in the claims shall not be construed as limiting the scope.

The invention claimed is:

1. An information interchange system comprising:
a reader, implemented through a computer processor, configured to extract, from a certificate obtained from a first health care facility at which the patient previously registered, a signature of a first service provider and a first identifier of the patient which is generated by the first service provider, and generate a second identifier of the patient corresponding to the first identifier, wherein the reader is at a second health care facility at which a patient is registering and the first identifier does not include the patient's real identity, but identifies the patient to the first health care facility;

a first identifier manager of the second health care facility configured to associate the first identifier with the second identifier and send a request to any one of a second identifier manager of the first health care facility and the first service provider so as to request a medical record associated with the first identifier; and a receiver of the second health care facility configured to receive the requested medical record from any one of the second identifier manager and the first service provider and associate the received medical record with the second identifier, wherein the second identifier manager further comprises:

an identifier mapping unit configured to map the first identifier to a third identifier;

a database configured to retrieve a record associated with the third identifier; and a sender configured to send the retrieved record to the receiver as being the record associated with the first identifier.

2. The information interchange system according to claim 1, further comprising:

a second service provider configured to generate identifiers; wherein any one of the reader and the first identifier manager is further configured to request a fourth identifier from the second service provider, and the reader is further configured to set the received fourth identifier as the second identifier.

3. The information interchange system according to claim 2, wherein the second service provider is further configured to generate a second certificate comprising a signature of the second service provider and the fourth identifier.

4. The information interchange system according to claim 3, wherein the reader is further configured to send the second certificate to at least one of the first identifier manager and the receiver.

5. The information interchange system according to claim 1, wherein the first identifier and the second identifier are pseudo identifiers generated by corresponding pseudonymization service providers, respectively, and the signature of the first service provider provides information about at least one of the second identifier manager and the first service provider.

6. The information interchange system according to claim 5, wherein the certificate further comprises a public key of a public key pair for checking the link between the certificate and the patient.

7. The information interchange system according to claim 5, wherein the certificate further comprises an additional dataset for checking the link between the certificate and the patient.

8. The information interchange system according to claim 7, wherein the link based on the additional dataset is checked offline.

9. The information interchange system according to claim 7, wherein the additional dataset is a hash of a secret s, wherein the s is any one of a predefined parameter known by the patient, the patient's personal information and his real identification.

10. The information interchange system according to claim 7, wherein the additional dataset comprises at least one biomedical parameter representing the patient's physiological character features.

11. A card for storing:

a certificate configured to identify a patient, wherein the certificate comprises:

a first pseudo identifier generated by a pseudonymization service provider and configured to be used in a health information management system, wherein the first pseudo identifier identifies a patient to a first health care facility at which the patient previously registered and does not include the patient's real identity, wherein the first pseudo identifier is mapped to a third identifier; and a signature of a pseudonymization service provider, configured to contain information about at least one of the pseudonymization service provider and an identifier manager, wherein the pseudonymization service provider generated the first pseudo identifier and the identifier manager is configured to identify the first pseudo identifier, retrieve a record associated with the third identifier, and send the retrieved record to a receiver as being the record associated with the first identifier.

12. The card according to claim 11, further comprising a public key of a public key pair for checking the link between the certificate and the patient.

13. The card according to claim 11, further comprising an additional dataset for checking the link between the certificate and the patient.

14. The card according to claim 13, wherein the additional dataset is a hash of a secret s, wherein the s is any one of a predefined parameter known by the patient, the patient's personal information and his real identification.

15. The card according to claim 14, wherein the additional dataset comprises at least one biomedical parameter representing the patient's physiological character features.

16. A method of obtaining information, the method comprising the steps of:

a) extracting, with a processor and from a certificate obtained from a first health care facility at which the patient previously registered, a signature of a first service provider and a first identifier of the patient which is generated by the first service provider, wherein the is processor at a second health care facility at which a patient is registering and the first identifier does not include the patient's real identity, but identifies the patient to the first health care facility;

b) generating, with the processor, a second identifier of the patient corresponding to the first identifier;

c) sending, with the processor, a request to any one of a second identifier manager of the first health care facility and the first service provider so as to request a medical record associated with the first identifier;

d) receiving, with the processor, the requested medical record from any one of the second identifier manager and the first service provider;

e) associating the requested medical record with the second identifier;

f) mapping the first identifier to a third identifier;

g) retrieving a record associated with the third identifier; and h) sending the retrieved record to a receiver as being the record associated with the first identifier.

17. The method according to claim 16, wherein the third identifier is any one of an identification number, a driver license number, an insurance number, and a registration number in a medical system.

18. The method according to claim 16, wherein the step of generating a second identifier comprises the steps of:

i.) sending a request to a second service provider so as to request the second identifier; and ii.) generating the second identifier corresponding to the first identifier by the second service provider.

19. The method according to claim 18, wherein the first service provider and the second service provider are pseudonymization service providers, and the first identifier and the second identifier are pseudo identifiers generated by corresponding pseudonymization service providers.

20. The method according to claim 18, wherein the step of generating a second identifier further comprises the step of generating a second certificate corresponding to the second identifier, wherein the second certificate comprises the signature of the second service provider and the second identifier.

21. The method according to claim 20, wherein the second certificate further comprises any one of a public key of a public key pair and an additional dataset for checking the link between the second certificate and a person holding the second certificate.

22. A method of generating a second certificate based on a first certificate, the method comprising the steps of:
   a) extracting, with a processor and from the first certificate obtained from a first health care facility at which the patient previously registered, a signature of a first service provider and a first identifier of the patient which is generated by the first service provider, wherein the processor is at a second health care facility at which a patient is registering and the first identifier does not include the patient's real identity, but identifies the patient to the first health care facility;
   b) checking the validity of the first identifier on the basis of at least one of the signature of the first service provider and the first identifier;
   c) generating the second certificate comprising a second identifier and signature of a second service provider, wherein the second identifier corresponds to the first identifier;
   d) mapping the first identifier to a third identifier;
   e) retrieving a record associated with the third identifier; and
   f) sending the retrieved record to the receiver as being the record associated with the first identifier.

23. The method according to claim 22, wherein the second certificate further comprises any one of a public key of a public key pair and an additional dataset, wherein any one of the public key of the public key pair and the additional dataset are configured to check the link between the second certificate and a person holding the second certificate.

24. The method according to claim 22, wherein the first service provider and the second service provider are pseudonymization service providers, and the first identifier and the second identifier are pseudo identifiers generated by corresponding pseudonymization service providers, respectively.

25. The method according to claim 22, further comprising the step of associating the record associated with the first identifier with the second identifier as being the record associated with the second identifier.

* * * * *